United States Patent [19]

Müller

[11] 4,442,889
[45] Apr. 17, 1984

[54] APPARATUS FOR COMBINED COOLING AND AERATION OF BIOCHEMICAL-ACTION VESSELS

[76] Inventor: Hans Müller, Im Almendli, Erlenbach/Zurich, Switzerland

[21] Appl. No.: 266,341

[22] Filed: May 22, 1981

Related U.S. Application Data

[60] Continuation of Ser. No. 966,132, Dec. 1, 1978, abandoned, which is a division of Ser. No. 837,706, Sep. 29, 1977, abandoned, which is a division of Ser. No. 559,362, Mar. 17, 1975, Pat. No. 4,073,696.

[30] Foreign Application Priority Data

Mar. 18, 1974 [CH] Switzerland .................. 3808/74
Sep. 10, 1974 [CH] Switzerland .................. 12389/74

[51] Int. Cl.³ .................................. F28F 13/12
[52] U.S. Cl. .................. 165/109 R; 261/93; 435/315; 435/316
[58] Field of Search ............ 165/108, 109; 195/142, 195/143; 261/93; 435/315, 316

[56] References Cited

FOREIGN PATENT DOCUMENTS

| 765295 | 6/1934 | France ................................ 261/93 |
| 54188 | 9/1955 | France ................................ 261/93 |
| 431566 | 7/1935 | United Kingdom .................. 261/93 |

*Primary Examiner*—Albert W. Davis, Jr.
*Attorney, Agent, or Firm*—Michael J. Striker

[57] ABSTRACT

A biochemical-action vessel accommodates a substrate in which biochemical reactions are caused by microorganisms. A heat-exchange arrangement is provided in the vessel and removes the heat generated in the substrate by such reactions. The substrate is circulated in the vessel advanced by an advancing arrangement in a closed path which passes through the heat-exchange arrangement. Aerating gaseous medium is introduced into the substrate upstream of the advancing arrangement and in the region of suction generated by the same, and entrained by the circulating substrate so as to supply the oxygen necessary for the aerobic growth of the microorganisms.

5 Claims, 13 Drawing Figures

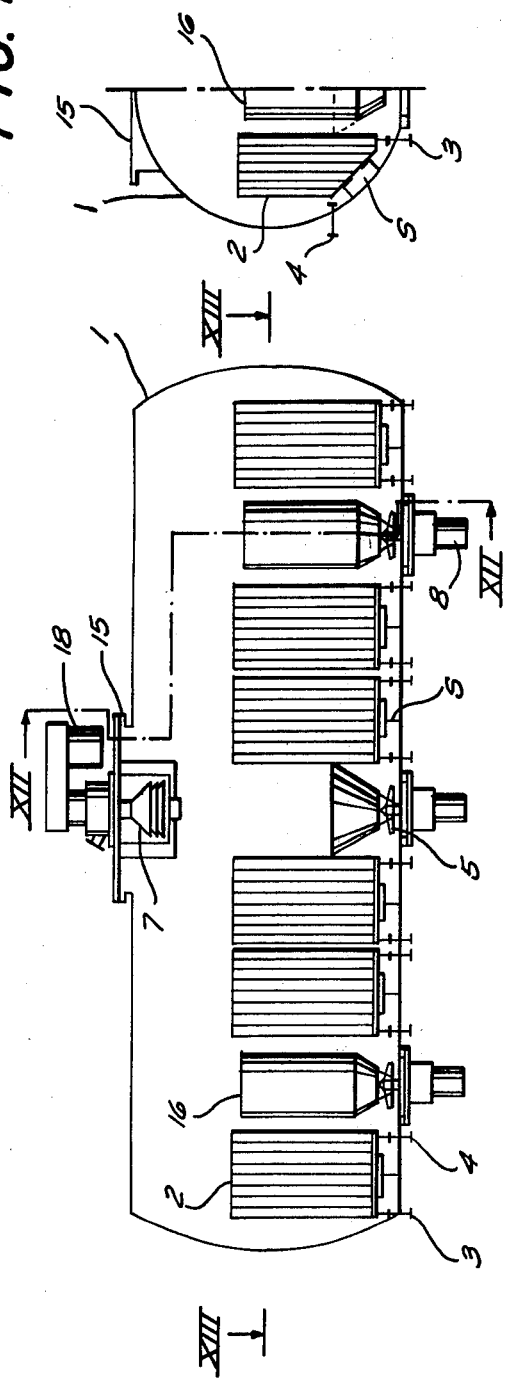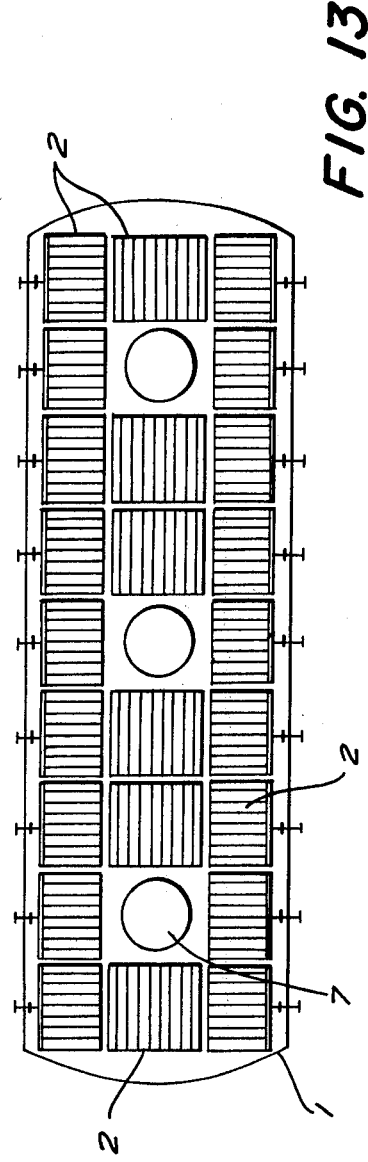

APPARATUS FOR COMBINED COOLING AND AERATION OF BIOCHEMICAL-ACTION VESSELS

This is a continuation of application Ser. No. 966,132, filed Dec. 1, 1978 now abandoned, which is a division of application Ser. No. 837,706, filed Sept. 29, 1977, now abandoned, which in turn is a division of application Ser. No. 559,362, filed Mar. 17, 1975, now U.S. Pat. No. 4,073,696 issued Feb. 14, 1978.

BACKGROUND OF THE INVENTION

The present invention relates to an apparatus for cooling and aerating the contents of a vessel, and more particularly to such an apparatus which is used for enhancing the biochemical action of microorganisms in such a vessel.

There are already known various arrangements for biochemically treating a substrate, such arrangements being used either for fermentation of the substrate, which is usually accomplished under anaerobic conditions, or for growing microorganisms, which is usually accomplished under aerobic conditions and where the substrate constitutes a nourishing medium. The present invention is concerned with the latter type of arrangements, especially such where the substrate is a body of liquid medium.

In the arrangements of this type, which employ biochemical action vessels in which the substrate is accommodated and acted upon by the microorganisms, there are encountered several problems. First of all, it is necessary to introduce substantial quantities of air into the substrate and to thoroughly mix the air with the substrate so as to enhance the biochemical action of the microorganisms and thus their growth. On the other hand, the biological action of the microorganisms results in liberation of substantial amounts of thermal energy, the biochemical reactions being exothermic, which thermal energy must be removed from the substrate in order not to interfere with the further growth of the microorganisms. Both of these problems must be solved in order to present a functioning biochemical action vessel of this type, and it has been heretofore difficult to solve these problems without involving excessive expenses in terms of capital investment and operating costs. This is due to the fact that the introduction of air into the substrate, as well as the deprivation of the latter of heat, required substantial amounts of energy. These increased costs are especially pronounced when the biochemical vessels are relatively large, in which case quantities in the order of several hundred cubic meters of air must be introduced into the vessel per minute, so that the air compressors used for delivering these substantial amounts of air must have a power input in the order of several thousand kilowatt, while cooling systems must be employed which have several thousand square meters of cooling area. All this considerably contributes to the significant cost of constructing and operating such an arrangement.

Various devices have already been proposed which are so constructed as to assure that the substrate will be sufficiently aerated while a sufficient amount of heat will also be removed from the substrate so that the biochemical reactions will be conducted under optimum conditions. Such devices are finding an ever-increasing application in the field of producing nutrient and fodder proteins, that is in the field of growing yeasts, bacteria and fungi. In the heretofore known devices, the problems of aerating the substrate on the one hand, and of removing heat from the substrate on the other hand, are for the most part solved independently of one another. Thus, for instance, there are already known high-output biochemical vessels in which the heat-removal process is accomplished outside the vessel in that the fluid medium or substrate is conducted to a heat exchanger located outside the vessel, while the substrate is supplied and mixed with the air needed for the biochemical reaction directly in the vessel. However, experience has shown that this is disadvantageous for at least two reasons: first of all, the microorganisms which are present in the substrate and carried with the same into the heat exchanger suffer in the latter an acute deprivation of oxygen, and secondly, circulation pumps are needed which have a very high throughput and, consequently, a high power consumption. On the other hand, the introduction of the air into the biochemical action vessel proper requires a high compressor output in terms of the quantity of the air delivered and the pressure differential to be overcome and, consequently, a high power input to such a compressor. This latter is due to the fact that the compressor has to overcome a relatively high static pressure of the substrate contained in the vessel, particularly since the air is usually introduced into the vessel in the bottom region thereof in order to assure sufficient aeration of the entire body of the liquid in the vessel.

Another disadvantage of the conventional arrangement of this kind is that the heat exchanger must be so constructed as to have several thousand square meters of surface area. This results in some other disadvantages, in addition to the substantial cost of such a heat exchanger. Thus, for instance, in many of the arrangements of this type a plurality of pipes is employed which connect the interior of the vessel with the exterior thereof and which also serve for conducting the fluid which is to exchange heat with the environment of the heat exchanger. With such an arrangement, it is extremely difficult to locate a leak if such should occur. Also, it is very difficult to periodically clean the heat exchanger so as to remove deposits of the microorganisms or other substances from the same.

SUMMARY OF THE INVENTION

It is a general object of the present invention to overcome the disadvantages of the prior art devices.

More particularly, it is an object of the present invention to provide an apparatus for cooling and aerating a substrate in a biochemical reaction vessel, which is not possessed of the drawbacks of the prior art devices of a similar kind.

It is a further object of the present invention to so construct the apparatus as to economize the operation thereof.

It is yet another object of the present invention to provide an apparatus for cooling and aerating the substrate, in which the microorganisms are not deprived of oxygen for any substantial periods of time.

In pursuance of these objects and others which will become apparent hereinafter, one of the features of the present invention resides, in an apparatus for cooling and aerating a substrate in a biochemical reaction vessel, In container means for receiving a fluid to be cooled and aerated, heat exchange means in the container means in contact with the fluid and operative for cooling the same, means for advancing the fluid through the heat-exchange means, and means for supplying aerating gaseous medium to the advancing fluid upstream of the advancing means. More particularly, the present invention resides in an apparatus in which the individual elements of the heat-exchange means are associated with pipes for introducing air or other gaseous medium into their vicinity, the end portions of the pipes being located in the region of suction generated in the fluid by the advancing means, so that the air introduced into the above-mentioned region is entrained by the circulating fluid.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWINGS

FIG. 11 is a longitudinal sectional view of a horizontal apparatus of the present invention;

FIG. 12 is a partial cross-sectional view of the apparatus taken on line XII—XII of FIG. 11; and FIG. 13 is a longitudinal sectional view of the apparatus taken on line XIII—XIII of FIG. 11.

DETAILED DISCUSSION OF THE PREFERRED EMBODIMENTS

Figure 1:
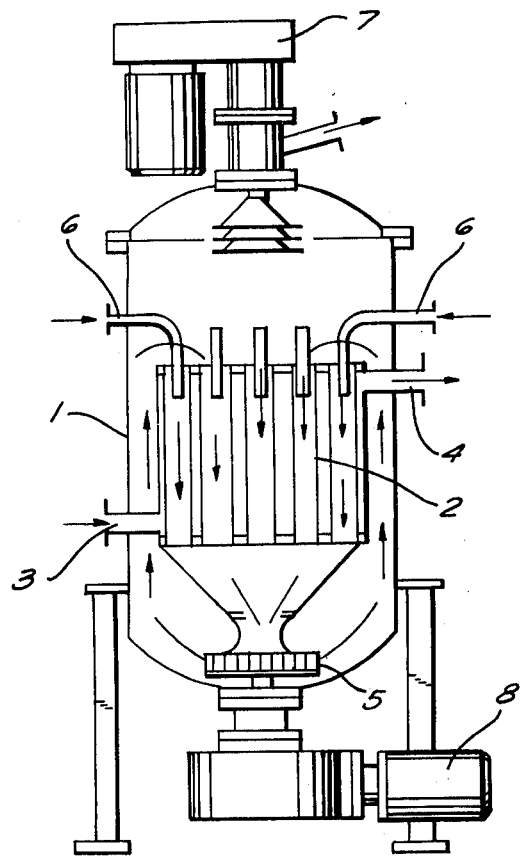
FIG. 1 is a longitudinal section of a cylindrical biochemical reaction vessel according to one embodiment of the invention.
Figure 2:
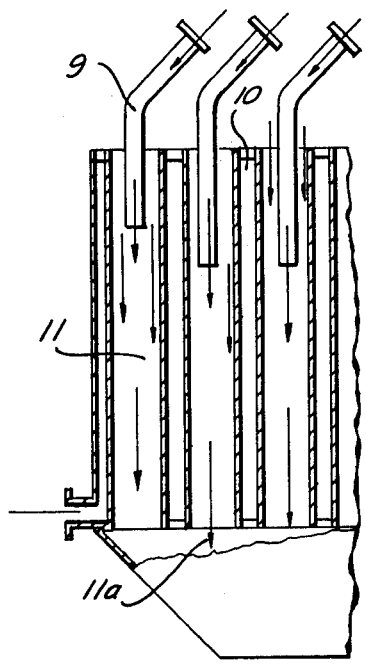
FIG. 2 is a detailed view similar to FIG. 1 showing in more detail the arrangement of the air-introducing pipes.

Referring now to the drawings in which the same reference numerals have been used for corresponding elements, and first to FIGS. 1 and 2 thereof, it may be seen that the reference numeral 1 designates a diagrammatically illustrated vessel the elongation of which extends in the upright direction. A heat exchanger 2 is accommodated in the vessel 1, and it can be constituted by a nest or array of parallel tubes, a helically coiled tube or a plurality thereof, or a plurality of tubes together constituting a plate-shaped heat exchanger. The heat exchanger 2 of this embodiment communicates with a cooling medium inlet pipe 3 and a cooling medium outlet pipe 4. A circulating or advancing arrangement 5, such as a pump of conventional construction, is located underneath the heat exchanger 2 and is driven into rotation by an electric or a similar motor 8. The purpose of the advancing arrangement 5 is to circulate the substrate accommodated in the vessel 1 from above to below and through the heat exchanger 5, and simultaneously to finely disperse the air or other gaseous medium in the substrate. The air or similar gaseous medium is introduced into the vessel 1, and more particularly into the substrate accommodated therein, through an air inlet pipe 6, and is distributed among a plurality of air introduction pipes 9 which are located between the various elements of the heat-exchanger 5. A mechanical froth separator 7 is provided in the upper portion of the vessel 1.

The substrate is advanced by the advancing arrangement 5 so that it flows radially outwardly of the latter and then upwardly along the walls of the vessel 1 and outwardly along the heat exchanger 2 until it reaches the uppermost portion of the latter, whereupon the substrate enters the heat exchanger 2 through the uppermost portion thereof. When the circulated substrate enters the heat exchanger 2 and flows through the same, drawn by the advancing arrangement 5, the air which is supplied to the air-introduction pipes 9 by the air inlet pipe 6 is entrained by the substrate and carried with the same. In one of the embodiments of the present invention, the pressure conditions in the vicinity of the outlet ends of the pipes 9 are such that subatmospheric pressure prevails in the pipes 9, so that the air is drawn into the pipes 9 and also into the pipe 6 from the exterior of the vessel without any need for employing a compressor or a blower at the inlet side of the pipe 6. Alternatively, the cross-section of the passages of the heat exchanger 2 in which the pipes 9 are located can be reduced in diameter so as to form a Venturi tube associated with each of the pipes 9, whereby the subatmospheric pressure prevailing in the pipes 9 and the pipe 6 is further reduced. Preferably, the advancing arrangement 5 is so dimensioned that the substrate flows through the heat exchanger 2 at a speed of between 0.5 and 3 meters per second from above to below. At this velocity, the entrained air bubbles are carried by the circulating substrate in the downward direction, independently of the particular height of the heat exchanger 2. The air-introducing pipes 9 can also be equipped with small nozzles or air-distribution filters.

When it is desired that the biochemical action vessel work under superatmospheric pressure, it is also necessary that the introduction of the air into the vessel be accomplished under pressure. Within the range of low and moderate superatmospheric pressures, and for high volumes of air which are required to accomplish the aeration procedure, it is possible to utilize a conventional blower which, as well known, requires for its operation much lower power input than a compressor which is to work at a pressure sufficient for overcoming the static pressure of the liquid in the vessel when the air is introduced at the bottom of the vessel.

FIG. 2 illustrates the arrangement of the air introducing pipes 9 in greater detail, as well as their location with respect to the elements of the heat exchanger 2. The liquid mixed with the air passes through a tube 11 and exits therefrom through the lower end 11a thereof. The cooling medium is circulated in the surrounding chambers 10.

Figure 3:
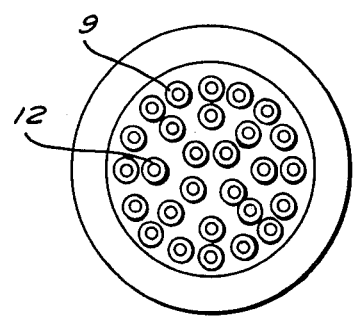
FIG. 3 is a top plan view of a heat exchanger of the tube-nest type to be used in the apparatus of the present invention.

FIG. 3 illustrates a heat exchanger 2 which utilizes a nest or an array of parallel pipes, in cross-section, wherein the air is introduced into the vessel 1 through the interiors of the pipes 9, while the cooling fluid circulates in the outer tube 12.

Figure 4:
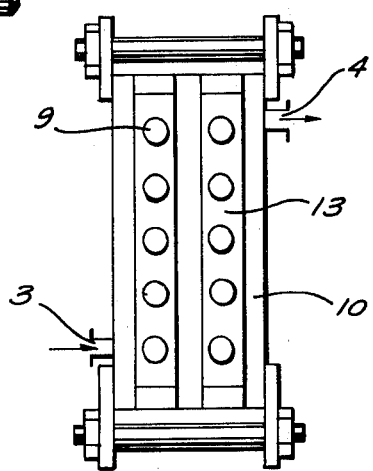
FIG. 4 is a cross-sectional view of a plate-type heat exchanger to be used in the apparatus of the present invention.

A plate heat exchanger is shown in cross-sectional view in FIG. 4. In this embodiment, the inlet 3 for the cooling medium is located in the lower part of the heat exchanger 2, while the outlet 4 for the cooling medium is located in the upper part of the same. The air-introducing pipes 9 communicate with circulation chambers 13 which are surrounded by chambers 10 for the cooling medium.

Figure 5:
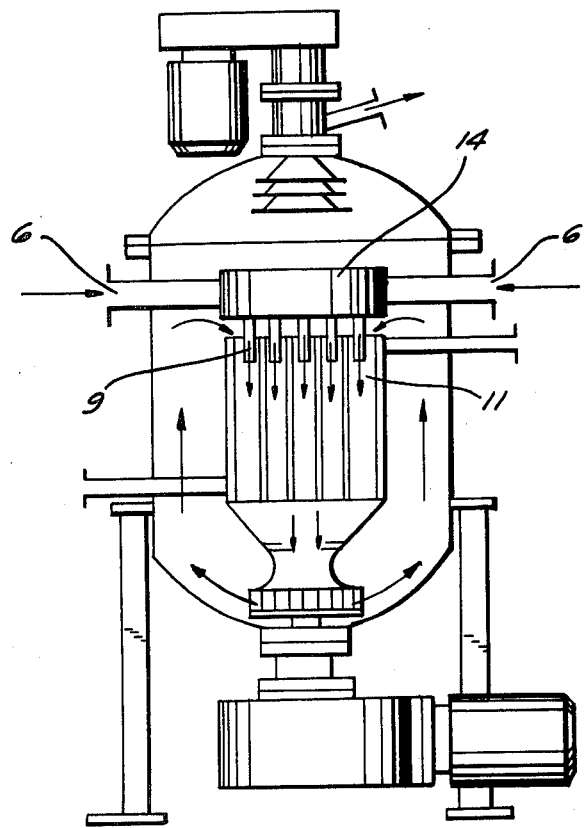
FIG. 5 is a longitudinal sectional view of a different embodiment of the apparatus of the present invention.

FIG. 5 illustrates a modification of the vessel 1 of FIG. 1, and particularly a modification of the air inlet system in which the air is first introduced into a distributor chamber 14 through two inlet pipes 6, and the air is then distributed into the plurality of the air-introducing pipes 9.

Figure 6:
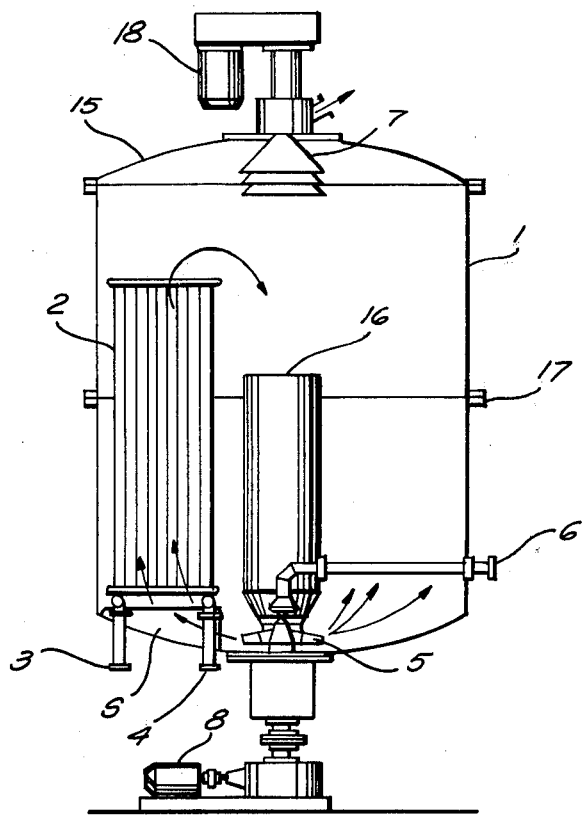
FIG. 6 is a longitudinal sectional view of another embodiment of the apparatus of the present invention.

A different embodiment of the biochemical action vessel 1 is shown diagrammatically in FIG. 6, wherein the vessel 1 accommodates in its interior segments or sections of the heat exchanger 2. The individual sections of the heat exchanger 2 are mounted on a support S which is, in turn, supported on the bottom of the vessel 1, so that the heat exchanger sections 2 are free to expand. This is particularly useful when the heat exchanger 2 is subjected to radically different temperatures, such as the temperature during the normal use when the heat exchanger 2 cools the substrate, and the temperature to which the heat exchanger 2 and the vessel 1, respectively, are subjected as a result of the action of hot water or steam, for instance during the sterilization thereof. The heat exchanger 2 is provided with the inlet pipe 3 and the outlet pipe 4 through which the cooling medium is introduced into and withdrawn from the heat exchanger 2 during the operation of the vessel 1. The biochemical action vessel 1 is provided with a lid 15 which renders possible placing, removing or replacing of the heat exchanger sections 2 therethrough without the need for disassembling the vessel 1 in its entirety. The circulating arrangement 5 is driven by means of an electric motor 8 of a conventional construction. A guiding tube 14 is located centrally of the vessel 1, and is connected thereto in any conventional manner. The aerating gaseous medium, such as air, is introduced into the interior of the vessel 1 through a pipe 6. The vessel 1 is constituted by an upper part and a lower part, which are connected by means of a flange 17 which can also serve for disassembling the vessel 1 by removing the upper part thereof. A mechanical froth remover 7 is accommodated in the upper part of the vessel 1, and is energized by an electric motor 18.

During the operation of the vessel 1, the circulating arrangement 5 generates a flow of the substrate through the sections of the heat exchanger 2, so that the fluid or substrate, after passing through the heat exchanger 2, enters the guiding tube 16 in the upper part thereof. The direction of flow is indicated by the arrows.

Since the vessel 1 is separated into two interconnected parts which are sealingly connected to one another by means of the flange 17, it is possible, when necessary, to lift the upper part of the vessel 1 after releasing the connection between the two parts of the vessel 1. This affords even better access to the various heat exchanger sections 2 than that afforded upon removal of the lid 15.

Figure 7:
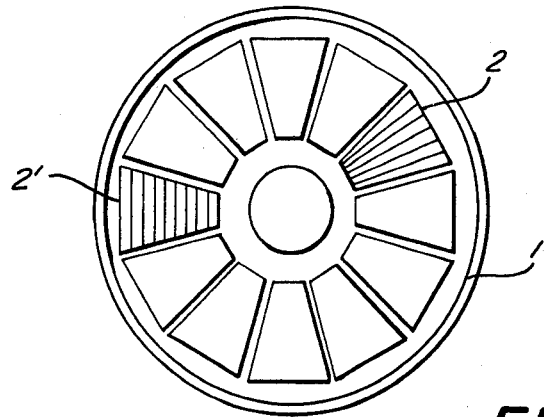
FIG. 7 is a diagrammatic cross-sectional view taken on line VII—VII of FIG. 6.

FIG. 7 illustrates a cross-sectional view of the vessel 1 of FIG. 6, showing particularly clearly the sectional construction of the heat exchanger 2. The sections of the heat exchanger 2 can be provided either with radially extending plates 2a, or with substantially circumferentially extending plates 2'.

Figure 8:
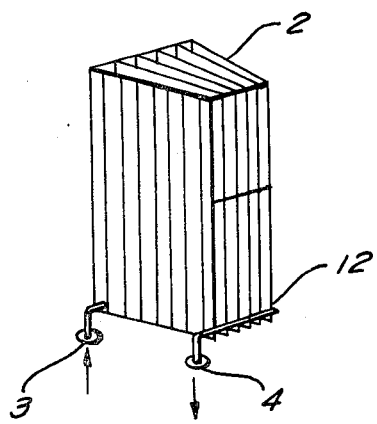
FIG. 8 is a perspective view of one section of the heat exchanger of FIGS. 6 and 7.

A single section of the heat exchanger 2 is illustrated in FIG. 8, having pipes 12 and the connecting pipes 3 and 4 for circulation of the cooling medium. The section of the heat exchanger 2 is constituted by a plurality of heat-exchange plates.

Figures 9, 10:
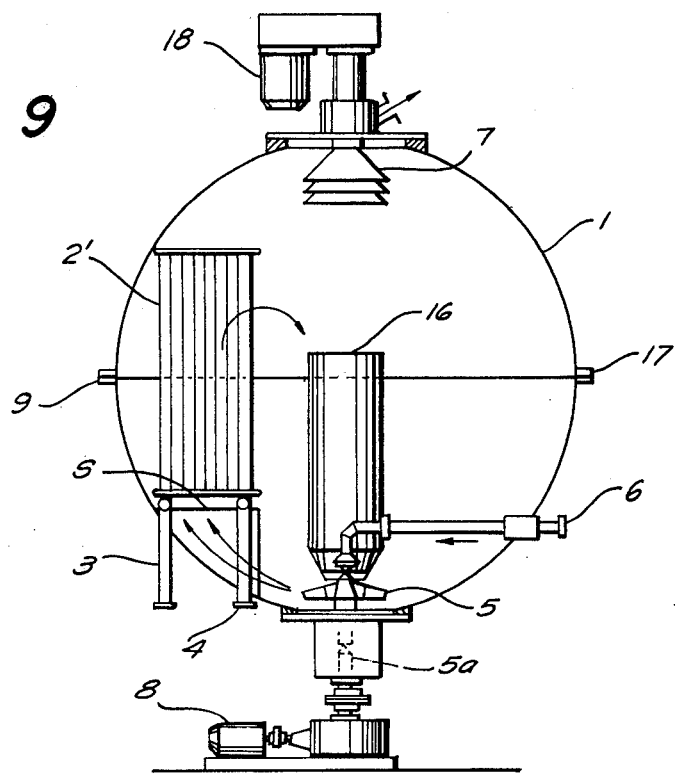
FIG. 9 is a longitudinal section of a spherical apparatus of the present invention.
FIG. 10 is a cross-sectional view of the apparatus according to the present invention taken on line X-X of FIG. 9.

A further embodiment, in many respects similar to the above-discussed embodiments, is illustrated in FIG. 9. Herein, the present invention is embodied in a spherical vessel 1. Here again, the heat exchanger sections 2 are accommodated in the interior of the spherical vessel 1, and supported on the supports S. Similarly to the above embodiments, the cooling medium is supplied to the heat exchanger 2 through the inlet 3 and withdrawn therefrom through the outlet 4. The substrate is circulated in the interior of the vessel 1 by means of the advancing arrangement 5 which is driven into rotation by an electric motor, so that the substrate passes in succession through the heat exchanger 2 and the guiding tube 16. The aerating medium, such as air, is introduced into the vessel 1 in the vicinity of the advancing arrangement 5 through the tube 6 or through a hollow shaft 5a on which the advancing arrangement 5 is mounted for shared rotation. The vessel 1 is again subdivided into two parts which are joined by a flange 17. When the upper part of the vessel 1 is removed, the heat exchanger 2 is easily accessible for inspection, repair and/or replacement purposes.

FIG. 10 illustrates a cross-sectional view of the vessel 1 of FIG. 9, wherein the heat exchanger 2 is constituted by a plurality of individual sections which may again be provided with radially or circumferentially extending cooling elements which have been explained in connection with FIG. 7.

FIG. 11 is a longitudinal section through a further embodiment of the present invention, in which the vessel 1 has the shape of a cylinder whose longitudinal axis extends substantially in the horizontal direction. A plurality of heat exchanger sections 2 is accommodated in the interior of the vessel 1, and these sections are again supported on supports S. In the upper region of the vessel 1, there is provided a relatively large lid 15 which covers an opening in that region which is so dimensioned that the individual sections of the heat exchanger 2 can be introduced into or removed from the interior of the vessel 1 therethrough. The guiding tube 16, which is illustrated in the right- and left-hand regions of FIG. 11 can be dispensed with when the heat-exchanger sections 7 are so arranged as to replace the guide tube 16 and to themselves serve for guiding the fluid toward the advancing arrangement 5, as illustrated in the central region of FIG. 11. The inlet pipes 3 and the outlet pipes 4 for the cooling medium are herin so arranged as to pass through the bottom of the vessel 1. The advantage of this embodiment, which is in all other respects similar to the above-discussed embodiments, is that a selected number of the advancing arrangements 5 can be accommodated in the interior of the vessel 1, the maximum number of such arrangements being determined only by practical considerations, such as the maximum dimensions of the vessel 1. Similarly to the previous embodiments, one or more froth separators 7 can be arranged in the upper region of the vessel 1.

FIG. 12 is a partial cross-sectional view of the biochemical action vessel 1 described in connection with FIG. 11, showing in more detail the arrangement of the sections of the heat exchanger 2, while FIG. 13 is another longitudinal section of the same vessel 1, this time taken in a horizontal plane and showing a top plan view of the heat-exchanger sections 2.

Experience with these novel biochemical action vessels as shown that it is possible to significantly simplify the construction of such vessels and thus to reduce the capital investment connected with the construction of such vessels. This is advantageously achieved by constructing the heat exchangers 2 as compact units which are accommodated in the interior of the vessel 1. In the currently preferred embodiments of the invention, the inlet and outlet pipes for the aerating gaseous medium and for the cooling medium are so arranged that they can be easily connected with and disconnected from the other elements of the assembly. Preferably, the inlet and outlet conduits pass through the bottom wall of the vessel 1. It is further currently preferred that the heat-exchanger sections 2 be mounted on supports S and connected thereto. In this manner, the various sections of the heat exchanger 2 can easily be inspected with respect to their fluid-tightness in the vessel which has been partially opened, for instance by removing the upper part therof, and also the sections can be easily cleaned and, when needed, replaced.

It will be understood that each of the elements described above, or two or more together, may also find a useful application in other types of aerating apparatus differing from the types described above. So, for instance, it is also possible to conduct the cooling and aerating operation in a container separate from the biochemical action vessel.

While the invention has been illustrated and described as embodied in an apparatus for cooling and aerating the substrate circulated in a biochemical action vessel, it is not intended to be limited to the details shown, since various modifications and structural changes may be made without departing in any way from the spirit of the present invention.

Without further analysis, the foregoing will so fully reveal the gist of the present invention that others can be applying current knowledge readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as now and desired to be protected by Letters Patent is set forth in the appended claims.

I claim:

1. An apparatus for cooling and aerating a substrate in a fermentation process, comprising a substantially cylindrical container elongated in a substantially horizontal direction and accommodating the substrate to be cooled and aerated; a plurality of heat-exchange sections located in said container and each including a number of parallel passages; means for advancing the substrate in said container in the direction of said passages; means for supplying gaseous aerating medium into said passages to be entrained by the substrate advancing through the passages; and said heat-exchange sections encircling said advancing means to provide a uniform aerating and cooling of the substrate through said elongated container.

2. A combination as defined in claim 1, and further comprising at least one support in said container means for supporting said heat-exchanger plates.

3. A combination as defined in claim 1 and further comprising a plurality of conduits for delivering cooling medium to said heat-exchanger plates; and wherein said conduits pass through the bottom of said container means and are dismountably connected thereto.

4. A combination as defined in claim 1 wherein said container means are provided with an opening in the upper region thereof; wherein said heat-exchanger plates are introduced into said container means through said opening; and further comprising lid means for closing said opening.

5. A combination as defined in claim 1, wherein said heat-exchanger sections include a plurality of interconnected cooling pipes.

* * * * *